US011331041B2

(12) United States Patent
Javitt et al.

(10) Patent No.: US 11,331,041 B2
(45) Date of Patent: May 17, 2022

(54) SYSTEM, METHOD AND COMPUTER-ACCESSIBLE MEDIUM FOR PREDICTING RESPONSE TO ELECTROCONVULSIVE THERAPY BASED ON BRAIN FUNCTIONAL CONNECTIVITY PATTERNS

(71) Applicant: The Trustees of Columbia University in the City of New York, New York, NY (US)

(72) Inventors: Daniel Javitt, Fort Lee, NJ (US); Joan Prudic, New York, NY (US); Stefan Rowny, New York, NY (US); Marta Moreno, Hopewell Junction, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 28 days.

(21) Appl. No.: 16/499,850

(22) PCT Filed: Mar. 30, 2018

(86) PCT No.: PCT/US2018/025457
§ 371 (c)(1),
(2) Date: Sep. 30, 2019

(87) PCT Pub. No.: WO2018/183887
PCT Pub. Date: Oct. 4, 2018

(65) Prior Publication Data
US 2020/0107777 A1 Apr. 9, 2020

Related U.S. Application Data (60) Provisional application No. 62/492,601, filed on May 1, 2017, provisional application No. 62/478,951, filed on Mar. 30, 2017.

(51) Int. Cl.
*A61B 5/00* (2006.01)
*G16H 70/60* (2018.01)
(Continued)

(52) U.S. Cl.
CPC ............ *A61B 5/4848* (2013.01); *A61B 5/055* (2013.01); *A61B 5/4064* (2013.01); *A61N 1/38* (2013.01);
(Continued)

(58) Field of Classification Search
CPC .............................. A61N 1/38; G01R 33/4806
See application file for complete search history.

(56) References Cited

U.S. PATENT DOCUMENTS 9,480,402 B2 11/2016 Leuthardt et al.
2008/0027346 A1* 1/2008 Litt .................... A61N 1/36064
600/544
(Continued)

FOREIGN PATENT DOCUMENTS

WO 2016089737 6/2016

OTHER PUBLICATIONS

European Search Report for European Patent Application No. 18775168.0 dated Feb. 18, 2021.
(Continued)

*Primary Examiner* — Edward Park
(74) *Attorney, Agent, or Firm* — Hunton Andrews Kurth LLP (57) ABSTRACT

An exemplary system, method and computer-accessible medium for determining an effect(s) of a convulsive stimulation therapy(ies) on a patient(s) can be provided, which can include, for example, receiving first information related to a visual network or a default mode network of a brain of the patient(s), receiving second information related to a subgenual ACC or a default mode (DMN network of the
(Continued)

brain of the patient(s), and determining the effect(s) of the convulsive stimulation therapy(ies) based on a relationship between the first information and the second information. The convulsive stimulation therapy(ies) can be an electroconvulsive therapy or a magnetic seizure therapy.

21 Claims, 6 Drawing Sheets

(51) Int. Cl.
| | |
|---|---|
| *G16H 30/20* | (2018.01) |
| *G16H 50/70* | (2018.01) |
| *G16H 50/20* | (2018.01) |
| *G16H 30/40* | (2018.01) |
| *G16H 20/70* | (2018.01) |
| *G06N 20/00* | (2019.01) |
| *A61B 5/055* | (2006.01) |
| *A61N 1/38* | (2006.01) |
| *A61N 2/00* | (2006.01) |
| *G01R 33/48* | (2006.01) |

(52) U.S. Cl.
CPC ......... *A61N 2/006* (2013.01); *G01R 33/4806* (2013.01); *G06N 20/00* (2019.01); *G16H 20/70* (2018.01); *G16H 30/20* (2018.01); *G16H 30/40* (2018.01); *G16H 50/20* (2018.01); *G16H 50/70* (2018.01); *G16H 70/60* (2018.01)

(56) References Cited

U.S. PATENT DOCUMENTS

| | | | |
|---|---|---|---|
| 2011/0184223 A1* | 7/2011 | Peterchev | A61N 2/006 600/14 |
| 2011/0301431 A1 | 12/2011 | Greicius et al. | |
| 2013/0113816 A1* | 5/2013 | Sudarsky | G06T 11/206 345/589 |
| 2013/0131438 A1 | 5/2013 | Brewer et al. | |
| 2015/0119689 A1* | 4/2015 | Pascual-Leone | A61B 5/055 600/410 |

OTHER PUBLICATIONS

Argyelan M et al., "Subgenual cingulate cortical activity predicts the efficacy of electroconvulsive therapy," Translational Psychiatry, vol. 6, No. 4, Apr. 1, 2016 (Apr. 1, 2016), pp. e789-e789.

Danilo Arnone et al, "Diagnostic and therapeutic utility of neuroimaging in depression: an overview," Neuropsychiatric Disease and Treatment, Aug. 1, 2014 (Aug. 1, 2014), p. 1509.

Redlich Ronny et al, "Prediction of 1-14 Individual Response to Electroconvulsive Therapy via Machine Learning an Structural Magnetic Resonance Imaging Data," JAMA Psychiatry, vol. 73, No. 6, Jun. 1, 2016 (Jun. 1, 2016), p. 557.

International Search Report and the Written Opinion dated Jun. 18, 2018 for International Application No. PCT/US2018/025457.

* cited by examiner

SYSTEM, METHOD AND COMPUTER-ACCESSIBLE MEDIUM FOR PREDICTING RESPONSE TO ELECTROCONVULSIVE THERAPY BASED ON BRAIN FUNCTIONAL CONNECTIVITY PATTERNS

CROSS REFERENCE TO RELATED APPLICATION(S)

The present application relates to and claims priority from International Patent Application No. PCT/US2018/025457 filed Mar. 30, 2018 which published as International Publication No. WO 2018/183887 on Oct. 4, 2018 and claims the benefit of U.S. Patent Provisional Patent Application Nos. 62/478,951, filed on Mar. 30, 2017, and 62/492,601, filed on May 1, 2017, the entire disclosures of which are incorporated herein by reference.

STATEMENT REGARDING FEDERALLY SPONSORED RESEARCH

This invention vas made with government support under Grant. Nos. MH096104 and MH090783, awarded by the National Institutes of Health. The government has certain rights in the invention.

FIELD OF THE DISCLOSURE

The present disclosure relates generally to electroconvulsive therapy, and more specifically, to exemplary embodiments of an exemplary system, method and computer-accessible medium for predicting response to electroconvulsive therapy ("ECT") based on brain functional connectivity patterns.

BACKGROUND INFORMATION

Previous work has examined the functional connectivity between different brain regions using standard functional brain imaging, or functional magnetic resonance imaging ("fMRI"). However, prior approaches could not accurately predict the effect of ECT on the brain of a patient. For example, some approaches can obtain a sensitivity of approximately 85%. Indeed, these prior approaches still miss approximately 15% of true responders, and would discourage greater than 20% of individuals from receiving ECT who might actually benefit from the treatment.

Electroconvulsive therapy ("ECT") has been proven to be one of the most effective last resort procedures in many psychiatric disorders within clinical trials. However, due to its side-effects, it is only prescribed for severely depressed patients who have failed to respond to antidepressants ("TRD") or may not be affected by pharmacological treatments. Remission rates of ECT are approximately 50%. The high efficacy for the most severe and refractory illness is combined with a shorter time to optimal response than required for antidepressants. Because of such efficacious record in clinical response, ECT can be a good candidate for early treatment of other illnesses such as severely agitated or suicidal patients. Despite its impressive efficacy, ECT carries a number of after-effects and risks. These side-effects include, for example, (i) confusion immediately after treatment, which can last from a few minutes to several hours, (i) memory loss causing trouble in remembering events that occurred right before treatment or in the weeks or months before treatment, (iii) physical side effects such as nausea, headache, jaw pain or muscle ache, and (iv) anesthesia runs the risks of medical complications such as heart rate and blood pressure increase, and in rare cases it can lead to serious heart problems.

ECT is known to be effective only in approximately 50% of individuals. Currently, the prescription of ECT can be driven by diagnostic and clinical indicators (e.g., APA, CANMAT, and NICE). The treatment can be most commonly recommended for unipolar or bipolar depression characterized by suicidal behavior, psychosis, catatonia, and/or resistance to psychotropic drugs. There are currently no guidelines to offer biologically-based predictors to more accurately predict response to ECT. To date, no biomarker with strong predictive characteristics has been developed. The practice of ECT would be significantly enhanced by a personalized approach based on biomarkers, which could precisely identify which patients are most likely to benefit from the treatment, thus optimizing the benefits against the risks of treatment for those who are candidates for ECT.

Thus, it may be beneficial to provide an exemplary system, method and computer-accessible medium for predicting response to electroconvulsive therapy based on brain functional connectivity patterns, which can be used to accurately predict the effect of ECT on the brain of a patient.

SUMMARY OF EXEMPLARY EMBODIMENTS

An exemplary system, method and computer-accessible medium for determining an effect(s) of a convulsive stimulation therapy(ies) on a patient(s) can be provided, which can include, for example, receiving first information related to a visual network of a brain of the patient(s), receiving second information related to a subgenual Anterior Cingulate Cortex network of the brain of the patient(s), and determining the effect(s) of the convulsive stimulation therapy(ies) based on a relationship between the first information and the second information. The convulsive stimulation therapy(ies) can be an electroconvulsive therapy or magnetic seizure therapy.

In some exemplary embodiments of the present disclosure, the effect(s) of the convulsive stimulation therapy(s) can be determined based on a connectivity between the visual network, the dorsolateral prefrontal network, and/or the subgenual ACC network. The connectivity can be a functional connectivity or an anatomical connectivity. The functional connectivity can be based upon functional brain imaging and alterations in the BOLD signal response. The anatomical connectivity can be based on white matter tracts in the visual network, dorsolateral prefrontal or the subgenual ACC network. The anatomical connectivity can be determined based on a diffusion tensor imaging procedure.

In certain exemplary embodiments of the present disclosure, third information related to a dorsolateral prefrontal cortex (DLPFC) of the brain can be received, and the one effect(s) of the convulsive stimulation therapy(ies) can be determined based on a further relationship between the first information and the third information. The DLPFC can be coupled to the subgenual ACC network. The DLPFC can also be negatively coupled to the subgenual ACC network. The effect(s) can be determined based on a visual covariate(s). The effect(s) can include a response of the patient(s) to the convulsive therapy(ies). The response can be a positive response. The first information and/or the second information can be received from a magnetic resonance imaging (MM) apparatus. The MM apparatus can be a functional MM apparatus. Third information can be generated based on the relationship between the first information and the second information, and the effect(s) can be determined by comparing the third information to fourth information related to a previous determination of the effect(s) on a plurality of further brains of a plurality of further patients. The second information can further include a default mode network of the brain of the patient(s).

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figure(s) showing illustrative embodiments of the present disclosure, in which.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figure(s) and the appended claims.

DETAILED DESCRIPTION OF EXEMPLARY EMBODIMENTS

The exemplary system, method and computer-accessible medium, according to an exemplary embodiment of the present disclosure, can utilize fMRI patterns between brain regions in a group of patients referred for ECT, and compare the patterns of functional connectivity in those patients who went on to benefit from ECT from those patients that did not benefit from ECT. A functional connectivity network can be defined using any of a number of parcellation procedures, including, for example, those defined using histological data (e.g. Brodmann map), those defined using functional connectivity (see, e.g., Reference 24) or those defined using multi-modal parcellation procedures. (See, e.g., Reference 24). A pattern of baseline connectivity can include two brain regions, one referred to as the subgenual Anterior Cingulate Cortex ("sgACC") and the other referred to as the dorsolateral prefrontal cortex ("DLPFC"), both of which can be used to predict patient response to ECT therapy.

The exemplary system, method and computer-accessible medium, according to an exemplary embodiment of the present disclosure, can include an integrated system to predict response to ECT based upon brain functional connectivity patterns, as determined, for example, using fMRI, although other imaging modalities can be used. The information obtained using the fMRI from a group of 18 subjects treated with ECT at Columbia/NYSPI was utilized. The exemplary system, method and computer-accessible medium, according to an exemplary embodiment of the present disclosure, can be used to predict with greater than 90% accuracy, which subjects would respond to ECT, and also to monitor the effectiveness of the treatment.

ECT has been believed as the "gold standard" treatment for depression, but nevertheless can be associated with significant side effects, including the need for general anesthesia, and memory loss for the period of the treatment, as well as memory loss for prior events. It may also induce remission of depression in only about 50% of individuals. Other individuals may only show a partial response. The exemplary system, method and computer-accessible medium, according to an exemplary embodiment of the present disclosure, can be used to predict which subjects can respond to ECT.

Approximately 100,000 patients receive ECT each year in the United States at a cost of about $20,000-50,000 per subject. In addition to the prediction of a response to ECT, the exemplary system, method and computer-accessible medium, can determine the number of treatments needed per each treatment course (e.g., typically patients receive multiple treatments over the course of weeks), and can be utilized to monitor patients during the course of their illness to determine when "maintenance" ECT can be beneficial. The exemplary prediction produced by the exemplary system, method and computer-accessible medium, can produce superior results when other measures can also be used, for example, connectivity involving only a specific portion of DLPFC (e.g., termed the "anticorrelated region" or "$DLPFC_{neg}$"), and when other brain networks including the Visual network and the Default Mode networks can be included.

The exemplary system, method and computer-accessible medium, according to an exemplary embodiment of the present disclosure, can thus be used to predict an exemplary treatment response. In addition, the exemplary system, method and computer-accessible medium can be utilized to monitor the treatment efficacy (e.g., determine how many treatments need to be given) and/or predict a potential relapse in patients who have previously responded to ECT.

Although both of the regions of the brain that can be utilized (e.g., sgACC and DLPFC) can be known to be involved in depression, only one subregion of DLPFC was previously determined to contribute to the prediction system, whereas other regions did not. In contrast, the exemplary system, method and computer-accessible medium, according to an exemplary embodiment of the present disclosure, can utilize information provided from multiple regions of the brain, whereby previously only one region was used, in order to obtain superior results.

The exemplary system, method and computer-accessible medium, according to an exemplary embodiment of the present disclosure, can be used to obtain and/or generate functional MRI information (e.g., using a computing device). Functional interconnection among brain regions, (e.g., among visual and default mode networks relative to dorsolateral prefrontal cortex) can be determined using such exemplary system, method and computer-accessible medium. A database of patterns associated with good versus poor outcomes from ECT can be generated and/or utilized thereby. The exemplary system, method and computer-accessible medium, according to an exemplary embodiment of the present disclosure, can refine predictions based on continually acquired information. The exemplary results can then be presented to clinician.

The exemplary system, method and computer-accessible medium, according to an exemplary embodiment of the present disclosure, can, for example, subdivide the frontal cortex into "correlated" and "anti-correlated" regions, and use, for example, the anti-correlated region. In addition, visual to frontal connectivity can also be considered/examined. Based on the above, the exemplary system, method and computer-accessible medium, can accurately predict responses in 92% of subjects, including all non-responders.

Using an exemplary model, the exemplary correlation between DLPFC and visual system can be p=0.005. The correlation strength can increase to p=0.0009 when other connections can be analyzed and taken into account, for example, by multivariate analysis. Thus, the exemplary system, method and computer-accessible medium, according to an exemplary embodiment of the present disclosure, can increase the predictive value of the magnetic resonance imaging ("MM") magnetic resonance ("MR") scan. In addition, the exemplary system, method and computer-accessible medium, can detect potential sources of error in the MRI MR scan including issues such as misalignment or motion.

The exemplary system, method and computer-accessible medium, according to an exemplary embodiment of the present disclosure, can reduce the number of individuals who turn out to be non-responders to ECT treatment from about 50% to greater than about 10%, while still identifying likely responders. Thus, the use of the exemplary system, method and computer-accessible medium, can save approximately 30,000 courses of treatment annually, which in turn can reduce health care costs by approximately $60-300M (e.g., in addition to reductions in patient inconvenience and side effects).

The exemplary system, method and computer-accessible medium, according to an exemplary embodiment of the present disclosure, can generate a database of patient information which can be used to analyze further patients. In addition to ECT, the exemplary system, method and computer-accessible medium, according to an exemplary embodiment of the present disclosure, can be used to optimize use of non-invasive treatments (e.g., other than ECT/MST), such as transcranial magnetic stimulation ("TMS") or transcranial direct electrical current stimulation ("tDCES"). Examples of tES include transcranial direct current stimulation ("tDCS"), transcranial alternating current stimulation ("tACS") and transcranial random noise ("tRNS") stimulation. These treatments use much lower energy than ECT, and do not cause seizures. However, they can also be less effective. Both TMS and tDCS tES can be administered in the fMRI, and the exemplary system, method and computer-accessible medium can be used to determine if a given placement stimulation approach can successfully remap the underlying circuits. When the correct locations per patient can be determined, subsequent treatments can be provided outside of the scanner.

Exemplary Cycle of Care

Patients with symptoms resembling depression can be presented to their primary care physician ("PCP") who can render diagnosis, and either prescribe the standard protocol of care for such patients, or depending on the severity of the symptoms, refer the patients to a psychiatrist. The standard psychiatric evaluation of the patients can be carried out according to DSM V after which the patient can be diagnosed with major depression disorder ("MDD"). Multiple drug classes exist for the treatment of MDD. While newer classes of medications can usually be the first line of treatment, older medications might be chosen, depending on the subtype of MDD, the age of the patient, cost considerations, and the practitioner's preferences. Most antidepressants have similar rates of efficacy overall, and time to onset of effectiveness (e.g., they all generally require 4-6 weeks to achieve maximum therapeutic benefit) (see, e.g., Reference 4), although can differ in terms of side-effect profiles.

Existing guidelines recommend four pharmacological strategies for the management of partial response or non-response of MDD: (i) increasing the dose of the antidepressant, (ii) switching to a different antidepressant, (iii) augmenting the treatment regimen with a non-antidepressant agent such as lithium, atypical antipsychotic drugs or thyroid hormones, or (iv) combining the initial antidepressant with a second antidepressant. (See, e.g., Reference 5). The patient can be continuously monitored by the psychiatrist. ECT can be considered for patients with severe MDD that may not be responsive to psychotherapeutic and/or pharmacological interventions, particularly those with significant functional impairment who have not responded to numerous medication trials. (See, e.g., Reference 6). The decision to recommend the use of ECT derives from a risk/benefit analysis for the specific patient. This analysis considers the diagnosis of the patient and the severity of the presenting illness, the patient's treatment history, the anticipated speed of action and efficacy of ECT, the medical risks and anticipated adverse side effects. These factors can be considered in making a determination to use ECT.

Patients with TRD can be divided into, e.g., two groups: (i) responders to ECT and (ii) non-responders to ECT. Potential responders can receive ECT with a higher degree of certainty about the outcome, and potential non-responders can be spared of the negative post-ECT after-effects, and can be directly committed to another treatment that would have otherwise had to wait based the response to the ECT treatment. Among the healthcare providers, a psychiatrist can use the exemplary system, method and computer-accessible medium and incorporate the new tool in their Pre-ECT Evaluation procedure to save their time and care for those patients who can certainly respond to ECT. Hospitals and private clinics can also spare the unnecessary resources that would be used to treat the non-responders patients, increasing the hospital utilization and positive outcomes, and insurance companies can save the unnecessary expense of an expensive treatments that may not improve the patients' condition. Further, society at large can be spared the substantial cost of futilely financing a treatment with no outcome, and harmful side effects.

One exemplary alternative for ECT can be TMS. TMS generally uses a specifically designed magnetic coil that can be placed in close proximity with the head to generate rapidly alternating magnetic fields and produce electrical stimulation of superficial cortical neurons. Based on the results of a multisite randomized sham-controlled clinical trial of high-frequency TMS over the DLPFC (see, e.g., Reference 7), TMS was cleared by the food and drug administration ("FDA") in 2008 for use in individuals with MDD who have not had a satisfactory response to at least one antidepressant trial in the current episode of illness. Initially, FDA approved a particular TMS device, called NeuroStar, manufactured by Neuronetics, Inc. In 2013, FDA approved another device, manufactured by Brainsway. In the years since FDA sanctioned the therapy, TMS treatment centers have been proliferating across the country. A typical course of TMS therapy involves 20 to 30 sessions, generally given in three to five treatments per week for four to six weeks. The full course of therapy with the pricey machines can cost $6,000 to $12,000. During the treatments, patients remain awake and alert, seated in a chair while a physician or a nurse places the device against the scalp. Slowly, insurance companies have begun to cover the non-invasive, though costly, treatments. However, plenty of questions about TMS still linger, including how best to deliver it, which patients make the best candidates, and even what exactly the device is doing in the brain. Despite these concerns, the therapy is gaining support from patients and mental health providers alike. Current guidelines have been drafted to direct rTMS at a site 5.5-cm anterior to motor cortex, called $M1_{hand}$, with threshold set at 120% of motor threshold. (See, e.g., Reference 8). Using this procedure, approximately 60% of patients who have failed to respond to a course of medication show beneficial response. (See, e.g., References 9-14). Nevertheless, efficacy remains below that of ECT.

There can be a limited number therapeutic options for TRD patients. One recently developed approach can be rTMS over left DLPFC. Recent studies have demonstrated overall antidepressant benefit of rTMS in patients who fail to respond to a trial of antidepressant medication. Nevertheless, for many patients, the response can be incomplete, suggesting the need for further optimization. One potential cause of heterogeneous response might be related to individual differences in brain anatomy and connectivity patterns. At present, the rTMS stimulation site across subjects can be based upon a fixed location relative to motor cortex. However, this approach can be optimized, for example, by stimulating based upon the individual's brain functional connectivity pattern. The exemplary system, method, and computer-accessible medium, according to an exemplary embodiment of the present disclosure, can be used to determine that the efficacy of TMS can be limited because the 5-cm rule does not guide TMS to the most effective location for each individual and that targeting based upon specific features of brain organization for each individual, can produce more robust and consistent results. Circuit-based targets can be an innovative approach to refine targeting for personalized TMS.

The exemplary system, method, and computer-accessible medium, according to an exemplary embodiment of the present disclosure, can also include and/or utilize non-invasive brain stimulation procedures. Millions of dollars have been invested in the development of these alternate treatments.

The exemplary system, method, and computer-accessible medium, according to an exemplary embodiment of the present disclosure, can be stored and encrypted on premises or in the cloud, and can be paired with a database of growing patient ECT and TMS outcomes that can drive an exemplary machine learning engine to improve the procedure consistently as more data can be collected. The exemplary input to this program (e.g., executed by and operating in a computer) can be provided through a website file upload or file transfer protocol ("FTP"), and can automatically be recognized as an MM output scan. The exemplary process can take approximately 24 hours to process the image and output the ECT efficacy or TMS targeting results in the form of a score or an image, respectively, which can then be sent back to the clinician in the form of a report. This time can vary based on multiple factors, and can be performed right before patient treatment. The exemplary procedure can compare each report against past efficacy data before it can be sent to the clinician.

Exemplary ECT

The exemplary system, method and computer-accessible medium, according to an exemplary embodiment of the present disclosure, can utilize fMRI FC patterns between brain regions from a group of patients that have already been treated with ECT, and categorized as responders vs. non-responders, can use such patterns to identify the patients referred for ECT treatment who can benefit from it from those who may not. The exemplary system, method and computer-accessible medium, according to an exemplary embodiment of the present disclosure, an use a pattern of baseline connectivity involving two brain regions—subgenual ACC "sgACC" and DLPFC—to predict treatment outcome with more than 90% accuracy. The exemplary system, method and computer-accessible medium can use FC of a specific portion of DLPFC (e.g., termed the "anti-correlated region" or "$DLPFC_{neg}$") which can be directly involved in the etiology of TRD. The exemplary PredECT uses $DLPFC_{neg}$, sgACC network, and/or visual network can be used to render its efficacy prediction. In addition, the exemplary system, method and computer-accessible medium, according to an exemplary embodiment of the present disclosure, can take any input image and monitor the effectiveness during the course of treatment, and assess the risk of a potential relapse in patients who have previously responded to ECT.

Exemplary TMS

The exemplary system, method and computer-accessible medium, according to an exemplary embodiment of the present disclosure, can also be used to guide an exemplary TMS treatment targeting to enhance its efficacy. A pattern of baseline connectivity involving the region more dysfunctionally connected to sgACC (e.g., the anti-correlated region of DLPFC or $DLPFC_{negs}$) for a new individualized TMS therapy can be used. The exemplary system, method and computer-accessible medium, according to an exemplary embodiment of the present disclosure, can operate on the basis of the hypothesis that the clinical efficacy of rTMS reflects FC between left DLPFC and remote regions such as the sgACC, and that the precise regions of DLPFC that can be functionally connected (e.g., anticorrelated) to sgACC can differ across individuals. Thus, individualized FC patterns using rsFC measures can assist in optimizing rTMS efficacy across individuals. Localizing $DLPFC_{neg}$ for each individual based upon pre-treatment rsFC, and then specifically targeting $DLPFC_{neg}$ can drastically improve outcome vs. standard non-personalized TMS (e.g., 5-cm rule).

Approximately 30% of individuals with MDD fail to respond to medication ("TRD"). For individuals with TRD ECT is the present gold-standard treatment but it can have limitations. Currently, 50% of patients undergoing ECT do not respond to their treatment. More than 30% refrain for seeking ECT treatment because of the risks and post-treatment effects. Despite these statistics, prior approaches could not accurately predict the effect of ECT on the brain of patient. Still miss approximately 15% of true responders, Prevents more than 30% of TRD patients who might actually benefit from receiving ECT.

The exemplary system, method, and computer-accessible medium, according to an exemplary embodiment of the present disclosure, can be used to predict an individual response to ECT (e.g., using fMRI).

The exemplary biomarker incorporated in the exemplary system, method and computer-accessible medium, according to an exemplary embodiment of the present disclosure, can, e.g.:

(i) reduce the number of non-responders from 50% to 5% or less by detecting 95%-100% of responders.

(ii) enhance the balance between risks and benefits in the decision-making process, and (iii) act as a reliable biological marker for a personalized-based medicine.

The value of the exemplary the exemplary system, method and computer-accessible medium can outweigh its cost to the system because the exemplary the exemplary PredECT can reduce the number of individuals who turn out to be non-responders to ECT treatment from 50% to approximately 5%, by identifying the likely responders. Additionally, the exemplary system, method and computer-accessible medium can save approximately 30,000 courses of treatment annually, which in turn can reduce health care costs by approximately $300M (e.g., in addition to reductions in patient inconvenience and side effects). Further, the exemplary The exemplary PredECT can cut in half the number of patients receiving ECT each year from 100,000 in the United States, providing a savings of approximately 1 to 2.5 billion dollars, considering a cost of about $20,000-50,000 per subject. The additional cost involving an MM would amount to about $200 million assuming an average cost of MRI scan to be $2,611. This means that the healthcare system can save about 800 million to 2.3 billion dollars annually.

The exemplary system, method and computer-accessible medium, according to an exemplary embodiment of the present disclosure, can be used to predict an individual response to ECT prior to its implementation. Such exemplary system, method and computer-accessible medium can use images of the brain to assess functional relationships between different brain regions to determine an effect(s) of a convulsive stimulation therapy on a patient. The exemplary system, method and computer-accessible medium, according to an exemplary embodiment of the present disclosure, can be an important and reliable predictor in the discrimination of responders vs. non-responders (e.g., >90% accuracy). Such exemplary system, method and computer-accessible medium can be a non-invasive procedure; patients may only need a standard functional MRI scan.

According to research by Healthnet updated in July 2016, major depression affects about 14-15 million adults, or approximately 5-8% of the adult population. Major depression, also known as MDD, unipolar depression, or clinical depression, can be a severe illness that results in significant disability and morbidity, and can be the leading cause of disability in many developed countries. More than about 60% of the individuals experiencing a major depressive episode ("MDE") can have additional MDEs as often as once or twice a year. If untreated, the frequency and severity of depressive illness increase, often leading to suicide. Standard treatments used can include a host of antidepressant drugs that can often be used as an alternative to or in conjunction with evidence-based psychotherapy. After failing 2 trials from different antidepressant drug classes, plus augmentation procedures, patients can be considered drug resistant and remission rates drop to about 20%. ECT can be the standard non-drug somatic therapy for depression. Other non-medication somatic therapies include vagus nerve stimulation ("VNS"), deep brain stimulation ("DBS"), and TMS. Electrical stimulation of neurons in regions of the brain responsible for mood is commonly used. VNS has not lived up to its original promise and the trials of DBS may not yet be conclusive enough for wide use of this invasive procedure.

ECT can be used to induce a rapid improvement in symptoms, but may have to be repeated over several sessions (e.g., usually 6-10) to prevent relapse. TMS does not require anesthesia or surgery, and can be performed on an outpatient basis, but typically can be repeated 5 times per week over the course of 4-6 weeks to achieve maximum response. On a patient basis, the following can be estimated: 14.5 million adults*60% victims with frequent MDEs*20% complete remission rate=1.74 million patients. The market in terms of procedure numbers, e.g., just taking ECT and conservatively assuming 6 sessions can be 1.74 million*50%+1.74 million*50%*6=6.09 million procedures (e.g., assuming that half of the patients can be diagnosed as not responsive to ECT). For TMS, it's potentially 1.74 million*40%*5 times per week*4 weeks+1.74 million*60%=14.96 million procedures. For example, for market size in terms of dollars reimbursed, if it can be assumed that, for example, about $442.77 is an approximation of willingness-to-pay for the similar digital analysis procedure mentioned in conjunction with CPT code 95957, and taking the smaller procedure numbers from ECT, the market size=6.09 million*$442.77=$2.7 Billion for just one use of the diagnostic tool before each ECT treatment. This can be the Total Addressable Market assuming only ECT can be considered for MDD patients, which can be a conservative estimate, given that ECT can also be used for other mental disorders.

Given the efficacy of the technology right now, even a market entrant would not detriment the growth of the captured market share substantially.

An exemplary device that can use or incorporate the exemplary system, method, and computer-accessible medium may not directly interact with the patient, which can only use the information from the patient, for example, fMRI maps and clinical assessment test results, can be used as an input to this diagnostic procedure. Thus, such exemplary device may not need FDA approval for common use in a "research" setting. Data from the 40 more subjects was generated to expand the patient population of proof-of-concept to vet the product, which can drive initial market acceptance and an even larger IRB-approved experiment. Existing data included (i) 18 patients treated by ECT used by the exemplary system, method and computer-accessible medium to correct efficacy assessment, (ii) IRB-approved study for treatment of 40 patients using the exemplary system, method and computer-accessible medium, and (iii) 100-200 patient study for rigor in the use of the exemplary system, method and computer-accessible medium. An exemplary strategy can be determined to secure market use approval on a "research" basis, based on the following principles: Accurate program specification can be provided in which the exemplary diagnostic tool can be described. Particular exemplary characteristics of the exemplary system, method and computer-accessible medium, which can be significant from an unmet need perspective, can be used to make an improvement in care of MDD patients compared to existing state of healthcare. The exemplary system, method, and computer-accessible medium, according to an exemplary embodiment of the present disclosure, can be used to identify patients who can respond to ECT treatment.

This exemplary determination can be made based on a brain network that can target MDD patients. fMRI sensitivity can be used for detection of brain networks involved in depression, and the exemplary system, method, and computer-accessible medium can predict responsiveness to the intended neuro-modulation by ECT.

In order to evaluate efficacy of the exemplary system, method, and computer-accessible medium, the following parameters exemplary ere used: 40 patients were enrolled with TRD over 1 year, and they were randomly assigned them to treatment with ECT using the exemplary system, method and computer-accessible medium to select patients based on personalized rsFC (e.g., group 1) or to the standard ECT procedure (e.g., group 2). All patients received MRIs at baseline, after $4^{th}$ session, after last session of ECT and at month 6 after completion of ECT treatments. Patients were monitored by psychiatrists, and followed for an additional period of 6 months. During the baseline inclusion visit, the inclusion/exclusion criteria were checked and participants were divided into two groups of 20 patients each. All patients in group 1 did their rsFC-map constructed on the baseline fMRI measurement to define their response to ECT using the exemplary PredECT. Upon completion of the MM scan, the rsFC was computed and patients with higher likelihood to respond to ECT (e.g., low $DLPFC_{neg}$ and sgACC network>−0.207) selected; the optimal cut-point was estimated from pilot data as responder>−0.20745. In group 2, patients followed the standard procedure. The exemplary system, method and computer-accessible medium, according to an exemplary embodiment of the present disclosure, (e.g., group 1) can differ from standard ECT (e.g., group 2) for: (i) prediction of treatment response to select patients who can benefit from ECT, (ii) determining the number of treatments needed per treatment course, and (iii) monitoring patients during the course of their illness to determine when "maintenance" ECT can be required. A Hamilton rating scale (e.g., HDRS-17) was also obtained at baseline and at the specific time points for analysis which included: baseline, after $4^{th}$ session, after last session of ECT and at month 6 after completion of ECT treatments. Raters were kept blinded to the treatment assignment.

After using the exemplary system, method and computer-accessible medium on group 1 or standard ECT on group 2, the responsiveness with HDRS-17 was assessed. The primary measure of efficacy can be the number of responders per group, defined by a decrease of at least 50% in the initial HDRS-17 score after last session of ECT and at month 6 after completion of ECT treatments. The number of treatments needed per subject at the end of each treatment course was recorded, and the number of remissions defined by a HDRS-17 score of <8 and HDRS item 1 (e.g., depressed mood) score=0 after last session of ECT and at month 6 after completion of ECT treatments was utilized. An increase in responsiveness to ECT in group 1 was seen compared to the existing 50% as an indication of success in this experiment. As such, a >80% responsiveness was obtained from the TRD patients who were selected for treatment by the exemplary system, method and computer-accessible medium. A lesser number of sessions per ECT course needed to achieve the expected response. Post ECT responders who maintain clinical response can be more likely to exhibit lower $DLPFC_{neg}$ at 6-month scan than those who relapse.

Exemplary Statistical Analysis

Prior to testing the exemplary system, method and computer-accessible medium, basic descriptive statistics were calculated using means and standard deviations, or proportions and per cents, as appropriate. The treatment groups were compared on such characteristics as age, gender, severity of depression, comorbid disorders; any difference which were included as covariates in outcome analyses. Handling of drop-outs and missing data: Missing data was imputed by interpolation (e.g., a subsequent data point exists) or last observation carried forward (e.g., no subsequent data point exists). All subjects having an initial MM and at least one pre-treatment evaluation were included in analyses involving initial MM only. All patients having a second MRI were included in all analyses.

Exemplary Analyses:

Mixed exemplary effect models were used with time (e.g., baseline, after last session of ECT), treatment group (remitter/non-remitter) levels: Additional time points (e.g. after $4^{th}$ session of treatment, month 6 after completion of ECT). The exemplary system, method and computer-accessible medium, standard ECT) and time by treatment group interaction as independent variables and HDRS-17 as a dependent variable. The time-by-treatment group interaction was tested at the 5% significant level and the change scores from the baseline to the four follow-up time points and their 95% confidence intervals were computed by two groups to guide future definitive trials. In addition, the time can be treated as a continuous variable and the non-linearity of the time trend was tested by adding quadratic and cubic terms of time. In addition, the sample can be divided by the baseline rsFC between $DLPFC_{neg}$ and sgACC network into two groups (e.g., high vs. low using the cutoff −0.207). Additionally, the three-way interaction between time, group and baseline rsFC group in the same mixed effect models was tested. The resulting three-way interaction suggests the moderation effect of baseline rsFC on the treatment.

Exemplary Power:

The attrition rate can be 10% over the 6 months' follow-ups, sample size of n=45 (e.g., n=55 per group) can result in n=100 (e.g., n=50 per group) completers in four weeks. Given the sample size of n=100, at least a moderate effect size of d=0.6 with 80% power at the 5% significant level being detected. A change in symptoms vs. change in biomarker was evaluated. Changes in HDRS-17 can correlate with change in rsFC in both groups, with larger symptom reduction correlated with greater change in rsFC. The study was powered to detect a moderate effect size correlation (e.g., r=0.28 in various groups.

Exemplary Analysis:

A time point of interest in the association can be provided after the last session of ECT (e.g., and at month 6 after completion of ECT treatments). Linear regression can be used with change scores in rsFC from baseline to last session of ECT, treatment group (e.g., two levels: The exemplary system, method and computer-accessible medium (and standard ECT) and their interactions as independent variables and changes in HDRS-17 as a dependent variable. The interaction between changes in rsFC and treatment group can be tested, which can be significant at 5% level. If it is not significant, the interaction term can be disregarded. In addition, e.g., the sample can be divided by the baseline $DLPFC_{neg}$ into two groups (e.g., high vs. low using the cutoff −0.207) and test the three-way interaction between change in rsFC, group and baseline rsFC group in the regression models can be tested. The resulting significant three-way interaction can indicate the moderation effect of baseline rsFC on the association between changes in symptoms and biomarkers. With the n=40 completers (e.g., n=44 recruited with 10% attrition rate), if the association between changes in rsFC and HDRS-17 can be at least r=0.28 in both groups, the association with more than 80% power at the 5% significant level can be detected.

The exemplary system, method and computer-accessible medium can also be used in parallel with ongoing studies with TMS. The targeting capability of the exemplary system, method and computer-accessible medium can be examined by using it with TMS to improve its efficacy by using personalized FC maps. An exemplary use of rsFC-MRI for TMS targeting can be based upon recent advances in understanding of brain FC in relationship to depression. This can be based on the recent finding that one of the regions more consistently linked to the pathogenesis of TRD based upon both structural and functional imaging can be the sgACC (e.g., BA25). (See, e.g., Reference 14). In healthy individuals, sgACC activity can be positively correlated with dorsal regions of DLPFC (e.g., approximately BA9) but negatively correlated with more ventral regions (e.g., approximately BA46). Although sgACC cannot be reached by TMS, it can be known to have strong FC with DLPFC, including both correlated and anti-correlated regions. The TMS over the left DLPFC can have distributed effects on deeper limbic regions such as the sgACC. (See, e.g., References 15 and 16). However, studies designed to investigate this hypothesis have produced conflicting results. (See, e.g., References 17-22). Here, the region can be connected in a more dysfunctional way to sgACC can be the anti-correlated region of DLPFC (e.g., $DLPFC_{neg}$, $DLPF_{neg}$) modified through a consideration of $DLPFC_{neg}$ to visual cortex connectivity, and therefore that TMS specific to the modified $DLPFC_{neg}$ region can be most effective. Alternatively, TMS can be applied to visual cortex, including dorsal, ventral, or MT+ parcellations.

The exemplary system, method, and computer-accessible medium, according to an exemplary embodiment of the present disclosure, can be based on and/or utilize the understanding that rsFC MM can improve spatial specificity and efficacy of TMS. The exemplary system, method and computer-accessible medium, according to an exemplary embodiment of the present disclosure, it can improve targeting in TMS, and expand its use not only in depression, but also for other conditions (e.g., OCD) where network-level targeting can be beneficial. $|_{(JD(1))}$In a recent ECT study, it was observed that, in TRD patients, rsFC between $DLPFC_{neg}$ and sgACC, the exemplary biomarker, was reduced. (See, e.g., FIG. 1).

Figure 1:
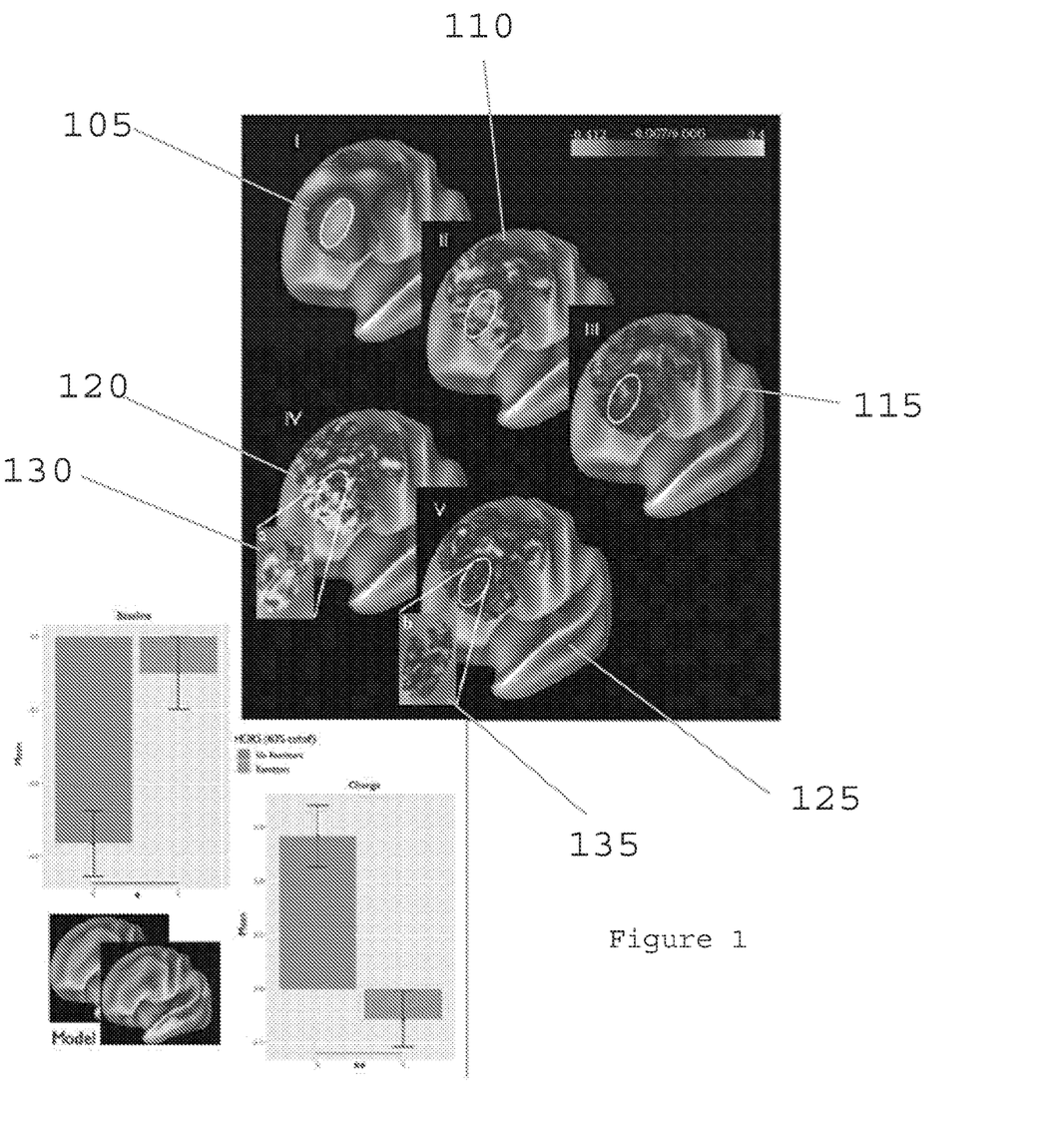
FIG. 1 is an exemplary diagram and an exemplary set of images of a subgenual connectivity with a negative region of the dorsolateral prefrontal cortex according to an exemplary embodiment of the present disclosure.

FIG. 1 shows the subgenual connectivity with the negative region of DLPFC, which can be based on a new biomarker for treatment response to ECT. Element 105 illustrates a SgACC connectivity map from 500 healthy subjects from HCP. Element 110 illustrates a baseline sgACC connectivity from non-responders. Element 115 illustrates a baseline sgACC connectivity from responders. A Change in sgACC connectivity from non-responders (post- vs. pre) is shown in element 120, which a negative region of DLPFC vales from non-responders (post- vs. pre) shown in element 130. Element 125 illustrates a change in sgACC connectivity from responders (post- vs. pre), with a negative region of DLPFC vales from responders (post- v. pre) shown in element 135. T-test baseline/change remitters vs. non-remitters can be *p=0.01, and **p=0.003, respectively. All sgACC connectivity maps are displayed over the left DLPFC. Shaded regions show surface vertices with negative correlation or positive correlation with the sgACC.

The exemplary biomarker may consider rsFC between DLPFCneg and visual regions, visual regions and DMN, and DLPFCneg and DMN, in addition to rsFC between DLPFCneg and sgACC, as well as connectivity within each of these regions. A reduction in the exemplary biomarker can predict ECT response (e.g., >90% accuracy) and can "normalize" following effective ECT. In addition, change in the exemplary biomarker can correlate with improvement, suggesting that it could be used to monitor treatment efficacy. Although both of the regions (e.g., sgACC, DLPFC) can be known to be involved in depression, only one subregion of DLPFC (e.g., $DLPFC_{neg}$) usefully contributes to the prediction whereas other regions do not. In addition, the predictive models can improve by incorporating visual cortex connectivity. The differential contribution was unexpected and (e.g., once confirmed in the ongoing project) could lead to an FDA-approvable procedure for targeting based on the individual brain FC pattern. (See, e.g., FIG. 2). This makes the exemplary biomarker a quantitative criterion on which the exemplary system, method and computer-accessible medium can be built which, for the first time, can offer a brain circuit based measure for predicting efficacy of neuromodulations in general and ECT and TMS in particular.

Figure 2:
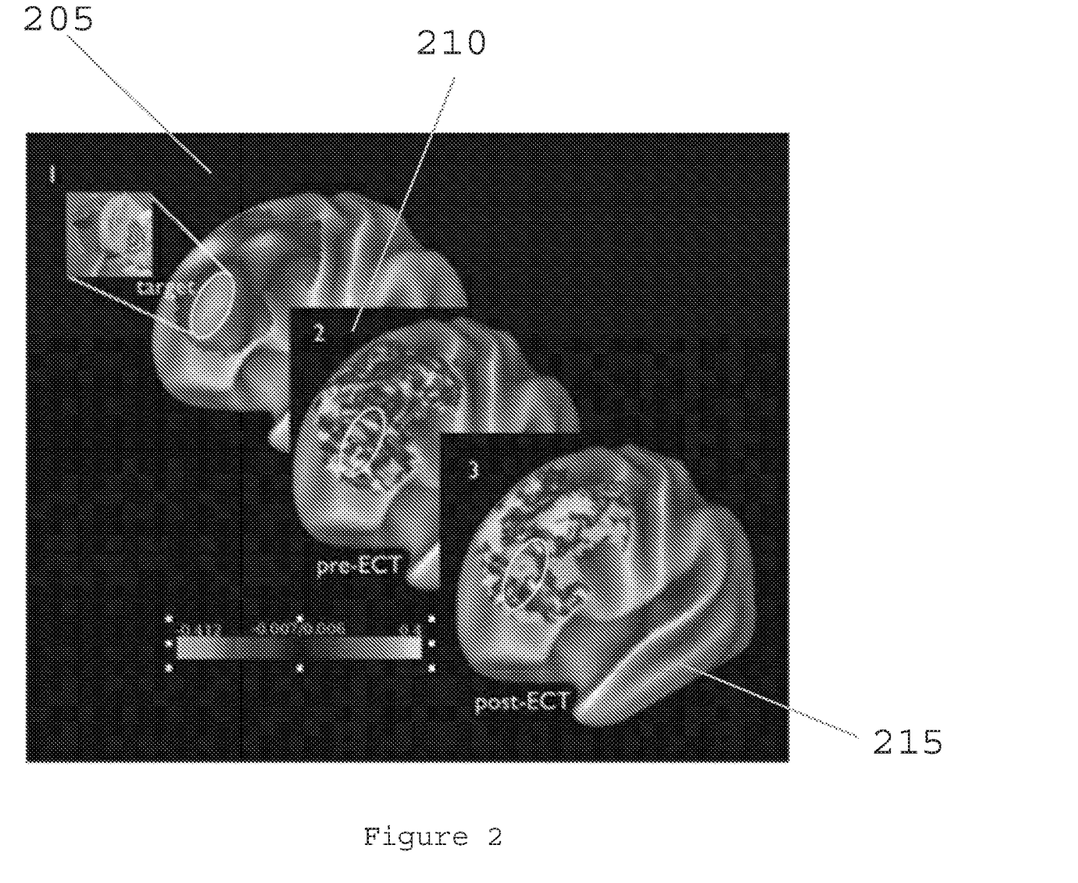
FIG. 2 is an exemplary set of images of a target for personalized rTMS according to an exemplary embodiment of the present disclosure.

FIG. 2 shows a target for personalized rTMS. The exemplary SgACC connectivity map from 500 healthy subjects is shown in element 205. The negative region of the DLPFC can be seen. A baseline sgACC connectivity with DLPFC for the subject with highest percentage change in depression after ECT is shown in element 210, which also shows individual targets. Element 215 shows an exemplary change in connectivity between negative region of DLPFC (e.g., hypothetical target) and sgACC after ECT. All sgACC connectivity maps are displayed over the left DLPFC. Shaded regions represent surface vertices with negative correlation or positive correlation with the sgACC. Additional TMS targets can include visual sensory regions (e.g. V1, early, dorsal, ventral, MT+)

Exemplary Prediction of ECT Response/Remission by RSFC Involving Visual Networks The exemplary system, method, and computer-accessible medium, according to an exemplary embodiment of the present disclosure, can be used for the evaluation using RSFC networks, including the visual cortex, to predict response and/or remission of depressive symptoms in TRD patients following ECT.

Exemplary Methods
  Exemplary Participants.
  Data were obtained from 18 TRD patients receiving ECT for clinical indications, with an age range of 18-65 and a mean of 51.7, who met DSM-IV criteria for a MDE according to the diagnostic assessment by the Structured Clinical Interview Patient Edition ("SCID-P"), with scores of 18 or greater (e.g., mean of 26.5) on the 24-Hamilton Depression Scale (e.g., HDRS-24). Patients with comorbid other Axis I or Axis II psychiatric disorders were excluded. All subjects were right-handed, and did not have severe medical conditions. Participants received a full course of right unilateral, frontal ECT. High resolution resting-state functional MRI ("rsfMRI") was collected pre/post ECT, and used for RSFC analyses. The Hamilton rating scale for depression (e.g., HDRS-24) was used to assess effectiveness of ECT treatment.
  Exemplary rsfMRI Acquisition.
  Anatomical and functional imaging data from each subject were collected and processed using acquisition guidelines and processing pipelines provided by the Human Connectome Project ("HCP"). High-resolution functional imaging scans were completed using a GE Discovery MR750 3.0 Tesla full body MR system equipped with a 32-channel phased array head coil.

Functional images were acquired with a GE-EPI sequence (e.g., 2.5 mm isotropic, slice plane=transverse, TR=2500 ms, SENSE factor=2, TE=22 ms, matrix=96×96, slices=54, phase encode=A→P). Images were transferred to a workstation with an HCP processing pipeline for analysis.

Exemplary RSFC Analyses.

Resulting structural and functional data were aligned in volume space to the MNI152 atlas, and in surface space to the HCP-generated Conte69 surface atlas. Resting-State data files underwent removal by regression of (i) CSF, (ii) white matter, (iii) whole brain, and (iv) movement parameters (e.g., 6 translation/rotation parameters+quadratic combinations of the 6 parameters+derivatives of these 12 parameters). To avoid slice-time correction affecting the movement parameters, movement parameters were derived from the data before HCP processing. Frames with FD>0.2 mm and/or DVARS with >(75 percentile)+(1.5)×(interquartile range) (fsl defaults) were then censored and interpolated, and a bandpass filter with a low cutoff of about 0.0005 Hz and high cutoff of about 0.2 Hz was applied. Subsequent analyses only used the non-censored frames (e.g., they did not include the interpolated frames).

Exemplary RSFC Analyses and Regions of Interest ("ROIs").

The sgACC ROI was constructed by placing an 8 mm radius sphere at MNI coordinates (e.g., 6, 16, −10). The sgACC ROI was used as a seed on an independent cohort of 500 healthy subjects from the HCP. The entire sgACC RSFC map was generated across 500 healthy subjects from the HCP dataset, which was used as a seed on the same sample. The DLPFC was omitted from the sgACC map to avoid biasing results toward increased sgACC-DLPFC connectivity. The exemplary sgACC-based seed map incorporated elements of default and limbic networks and ventral-attention networks.

The sgACC-based map was used as a seed in the same sample of healthy subjects to locate regions with the highest negative correlation with the DLPFC. These negative areas within the DLPFC were used to create our DLPFCneg masks. The exemplary sgACC-based seed map was applied to the sample of 18 TRD patients undergoing ECT. DLPFCneg masks were used to extract the mean average correlation with the sgACC.

Regional analyses were performed using a multi-modal parcellation procedure of the human cerebral cortex. (See, e.g., Reference 24). Specific analyses investigated predictive utility of RSFC between DLPFC and (i) sgACC, (ii) default mode network ("DMN") and (iii) visual cortex, as well as RSFC within each of these networks.

Exemplary Statistical Analyses.

Correlational analyses were performed to examine the degree to which RSFC within specific networks predicted degree of change in HDRS score both pre and post ECT. Categorical analyses were used to evaluate the degree to which RSFC measures could be used by the exemplary system, method, and computer-accessible medium to predict the degree to which a given individual would be a responder to ECT, and the degree to which they achieved full symptom remission. To determine prediction and neural mechanism of response, treatment response was defined as 50% or more reduction in symptoms, and remission was defined as final HAM-D score<7.

Specific ROIs included in, for example, the analysis consistent of DLPFC areas 46 and P9-46v, sgACC area 25, DMN areas a24 and s32, and visual areas MT+, V1, early visual, ventral and dorsal regions. For each main predictor, or underlying mechanism, in the exemplary regression models, AUC of the ROC curve with a 95% confidence interval was computed. All statistics were two-tailed, with preset alpha level for significance of p<0.05.

Exemplary Results.

Using the exemplary system, method, and computer-accessible medium, according to an exemplary embodiment of the present disclosure, a significant correlation was observed between DLPFC area 46 and both sgACC (e.g., r=0.54, p=0.02) and DMN area a24 (e.g., r=0.58, p=0.01), and between DLPFC area p9-46v and DMN area a24 (e.g., r=0.52, p=0.03). However, exemplary prediction models based upon these connections alone, or in combination, did not fully predict ECT response. (See, e.g., Table 1, Models 1-3). A significant correlation was also observed between DLPFC area 24 to DMN area s32 RSFC and clinical response (e.g., r=0.69, p=0.002), but was only partially predictive of recovery. (See, e.g., Table 1, Model 4).

When RSFC was assessed between DLPFC and visual regions using the exemplary system, method, and computer-accessible medium, as well as within visual regions, unexpected results were obtained. When RSFC between DLPFC p9-46v and visual MT+ was used as a predictor, the degree of correlation (e.g., r=0.61, p=0.007) and predictive value (see, e.g., Table 1, Model 5) were as good, or better, than those for traditionally applied networks involving sgACC or DMN.

Figure 3A:
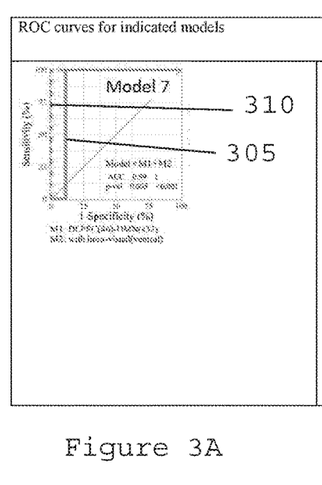
FIGS. 3A-3C are exemplary graphs of receiver operating characteristic curves for the exemplary system, method, and computer-accessible medium according to an exemplary embodiment of the present disclosure.
Figure 3B:
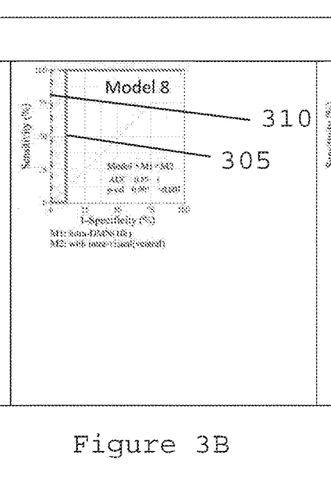
Figure 3C:
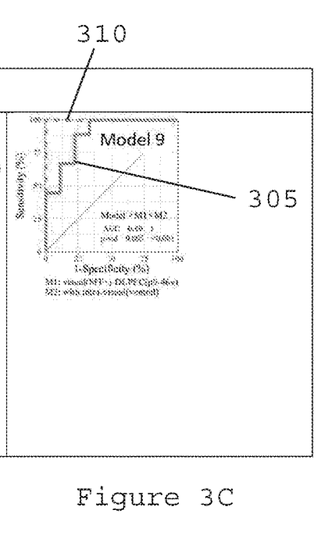

Connectivity within the visual ventral network also was highly predictive. (See, e.g., Table 1, Model 6). Further, as opposed to combination models involving DLPFC and both sgACC and DMN (see, e.g., Table 1, Model 2) that were only partially predictive, exemplary models involving DLPFC, DMN and visual cortex (e.g., the exemplary system, method, and computer-accessible medium) were fully predictive of response. These included exemplary models that included connectivity within the visual ventral stream combined with DMN (see, e.g., Table 1, Models 7 and 8), as well as exemplary models that involve only DLPFC and visual regions, without involvement of either DMN or sgACC (See, e.g., Table 1, Model 9) or exemplary models that involve only visual regions (See, e.g., Table 1, Model 10-11). FIGS. 3A-3C show exemplary graphs of exemplary models 7-9. As shown therein, exemplary Models 8, 9 and 10, FIGS. 3A, 3B and 3C, respectively, illustrate the sensitivity versus specificity for Ml: intra-DMN (e.g., element 305) and M2: with intra-visual (e.g., element 310). Other visual regions, including dorsal (see, e.g., Table 1, Model 10) and MT+(see, e.g., Table 1, Model 11) were also unexpectedly predictive of response/remission following ECT.

As detailed above, the exemplary system, method, and computer-accessible medium, according to an exemplary embodiment of the present disclosure, can be used to predict patient response to ECT. For example, visual connectivity can be used by itself to predict response to ECT as well as models involving sgACC and DMN. Additionally, a 100% predictivity can be obtained from simultaneous models that can use DLPFC and visual cortex, even without the use of either sgACC or DMN. Thus, the exemplary system, method, and computer-accessible medium, according to an exemplary embodiment of the present disclosure, can utilize the connectivity within visual cortical regions, including but not limited to, (i) ventral, (ii) dorsal and (iii) MT+ regions in the prediction of ECT response. Therefore, the exemplary use of visual connectivity in combination with connectivity involving other brain networks such as DMN, can be beneficial.

Although the description herein discusses utilizing a particular parcellation procedure (see, e.g., Reference 24), it should be understood that other exemplary parcellation procedures can be used, and are in the scope of the present disclosure. (See, e.g., Reference 23).

Exemplary Model

Table 2 compares the exemplary models used by the exemplary system, method and computer-accessible medium and previously-used models. For example, all models can be based on prediction of a 50% improvement in the clinical 17-item Hamilton Rating Scale for Depression ("HDRS-17"). This can be a commonly used criterion of treatment response. Results can be shown based on a logistic regression analysis across 10 subjects. $R^2$ and adj $R^2$ values can be based on logistic regression and illustrate how strongly the connectivity measures predict response. The exemplary p-values can be the statistical probabilities associated with the $R^2$ values. The AUC can be a measure of how well the model distinguishes responders and non-responders, with 1 representing perfect separation.

TABLE 2

| Model | Model components | $R^2$/ Adj. $R^2$ | p-value | $AUC^2$ |
|---|---|---|---|---|
| 1 | DLPFC(combined pos/neg regions) to sgACC connectivity Visual covariates not included | 0.0053/−0.1945 | 0.82 | 0.50 |
| 2 | DLPFC (combined pos/neg regions) to sgACC Visual covariates included | 1.00/0.20 | 0.04 | 1 |
| 3 | DLPFC (combined pos/neg regions)_Visual connectivity Visual covariates included | 1.00/0.20 | 0.04 | 1 |
| 4 | DLPFC (negative region only) - sgACC No covariates | 0.34/0.15 | 0.07 | 0.94 |
| 5 | DLPFC (negative region only) - sgACC Visual convariates included | 1.00/0.20 | 0.04 | 1 |

[1]Visual convariates include: visual to DMN, visual to frontoparietal & DMN to frontoparietal
[2]AUC: Area under the curve, logistic regression model.

Exemplary Model 1 described in Table 2 is the exemplary default model previously used (see, e.g., Reference 12) in which connectivity between DLPFC and sgACC was considered. However, Model 1 cannot accurately predict a patient's response to ECT. Exemplary Model 2 described in Table 2 can examine FC involving visual regions. With exemplary these regions included, Exemplary Model 2 can increase the prediction of treatment response. This was unexpected. Exemplary Model 3 described in Table 2 can include the visual covariates, which can achieve superior results even without the inclusion of DLPFC-sgACC. This can also be unexpected, and can suggest that DLPFC—visual connections can be more important than DLPFC to sgACC (e.g., contrary to prior models). Exemplary Model 4 described in Table 2 can utilize a different definition of DLPFC in which only the subregion of DLPFC that can be negatively coupled to sgACC can be considered (e.g., "anti-correlated region" or "$DLPFC_{neg}$"). This exemplary region, while previously described as being useful for predicting target location for TMS (see, e.g., Reference 13), has not been used as a correlate for ECT. Exemplary Model 5 described in Table 2 illustrates results achieved by including visual covariates to Exemplary Model 4, which can lead to an increase in the prediction rate. As provided in exemplary Models 2-5, this exemplary method can predict ECT response by considering connectivity between visual regions and DLPFC in addition to (e.g., or instead of) DLPFC to sgACC. The $DLPFC_{neg}$ and can also be used to increase the prediction rate. An exemplary approach can be to include the visual covariates and, in addition, to include only the $DLPFC_{neg}$. This can be used in the exemplary system, method and computer-accessible to predict ECT response and calculate TMS targets.

Figure 4A:
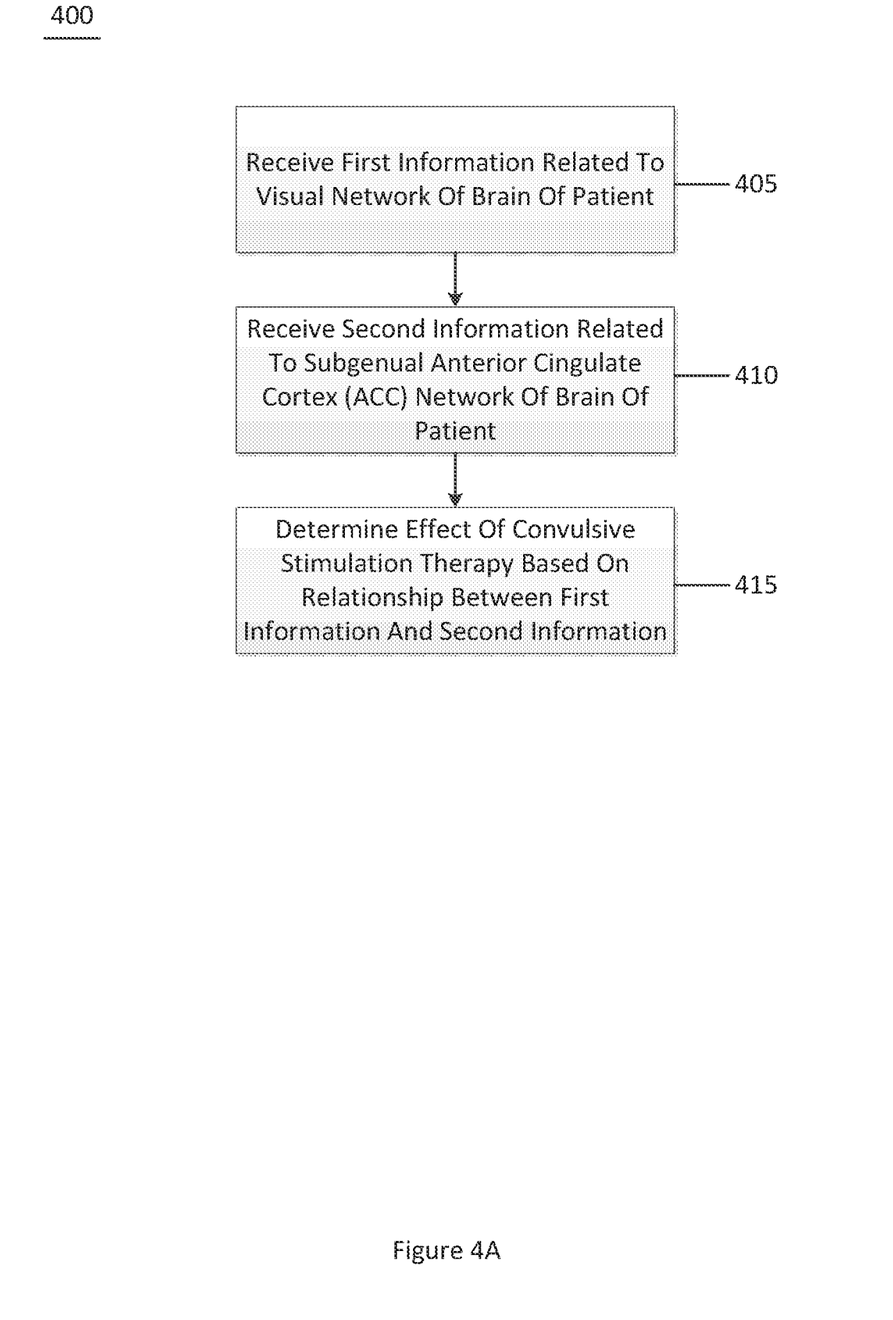
FIG. 4A is an exemplary flow diagram of an exemplary method for determining an effect of a convulsive stimulation therapy on a patient according to an exemplary embodiment of the present disclosure.
Figure 4B:
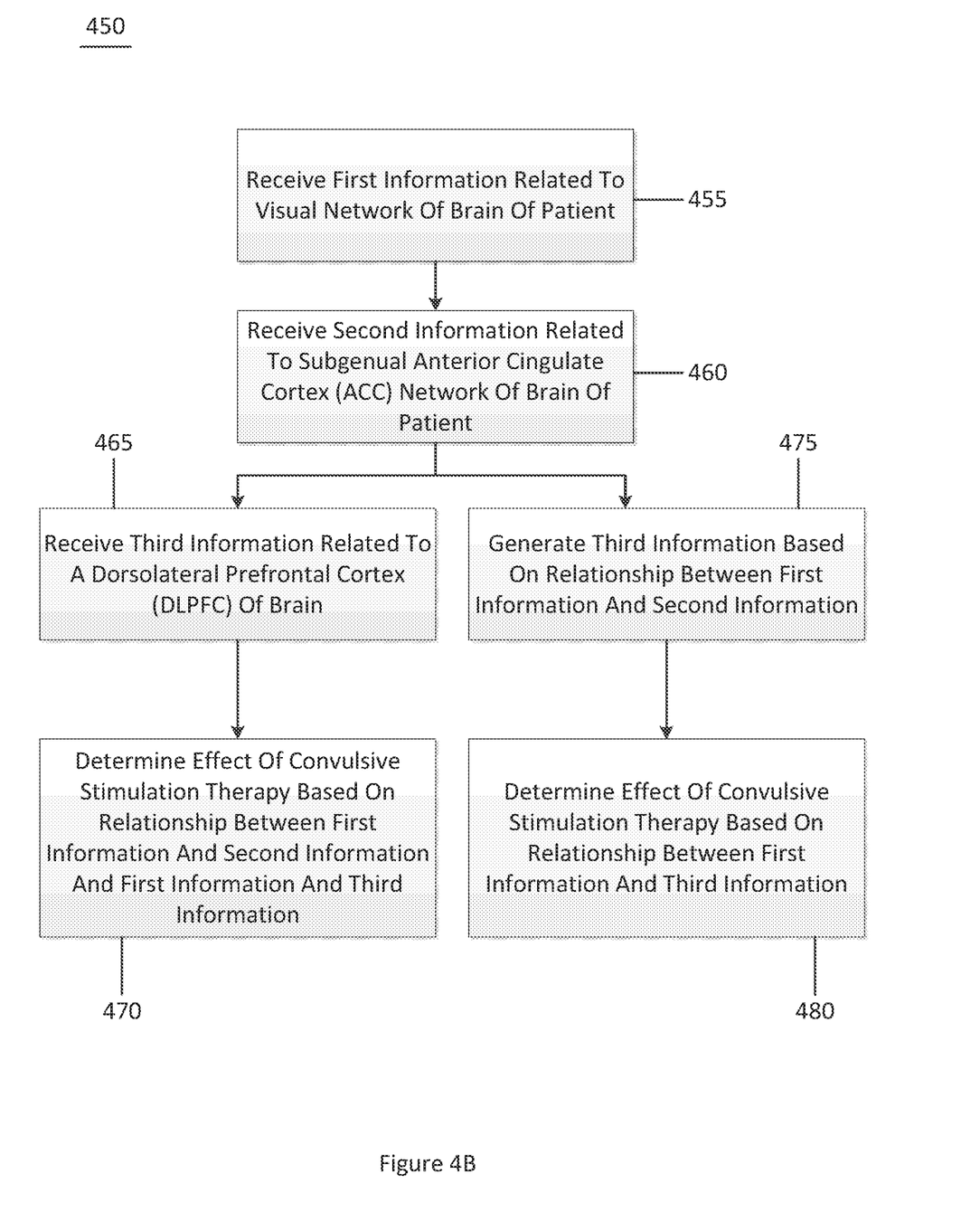
FIG. 4B is a further exemplary flow diagram of a further exemplary method for determining an effect of a convulsive stimulation therapy on a patient according to an exemplary embodiment of the present disclosure.

FIG. 4A shows an exemplary flow diagram of an exemplary method 400 for determining an effect of a convulsive stimulation therapy on a patient according to an exemplary embodiment of the present disclosure. For example, at procedure 405, first information related to a visual network of a brain of the patient can be received. At procedure 410, second information related to a subgenual ACC network of the brain of the patient can be received. At procedure 415, the effect of the convulsive stimulation therapy can be determined based on a relationship between the first information and the second information FIG. 4B shows a further exemplary flow diagram of a further exemplary method 450 for determining an effect of a convulsive stimulation therapy on a patient according to an exemplary embodiment of the present disclosure. For example, at procedure 455, first information related to a visual network of a brain of the patient can be received. At procedure 460, second information related to a subgenual ACC network of the brain of the patient can be received. At procedure 465, third information related to a DLPFC of the brain can be received, and at procedure 470, the effect of the convulsive stimulation therapy can be determined based on a relationship between (i) the first information and the second information and (ii) the first information and the third information. Alternatively, e.g., after procedure 460, third information can be generated based on a relationship between the first information and the second information at procedure 475. Then, at procedure 480, the effect of the convulsive the stimulation therapy can be determined based on a relationship between the first information and the third information.

Figure 5:
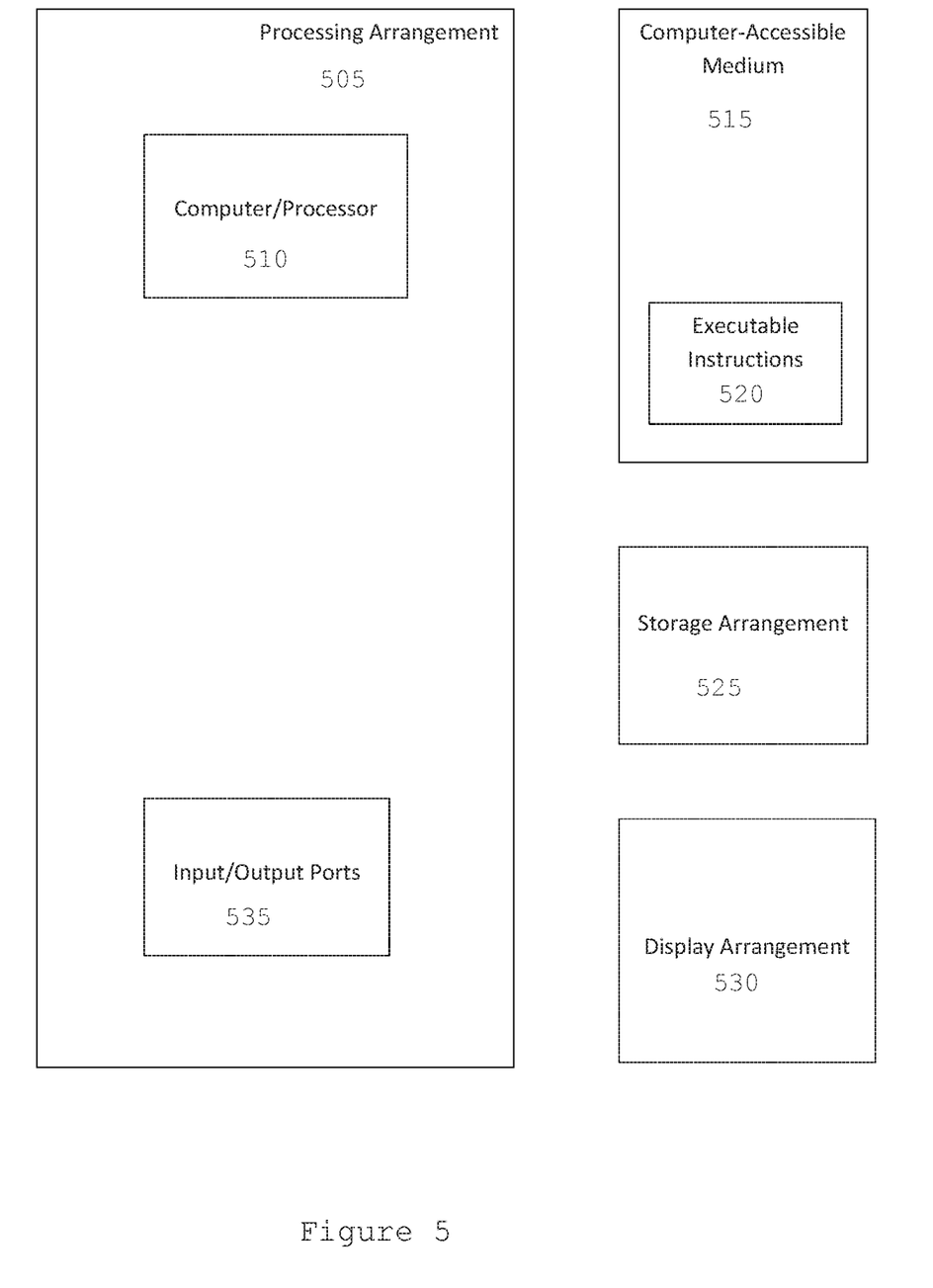
FIG. 5 is an illustration of an exemplary block diagram of an exemplary system in accordance with certain exemplary embodiments of the present disclosure.

FIG. 5 shows a block diagram of an exemplary embodiment of a system according to the present disclosure. For example, exemplary procedures in accordance with the present disclosure described herein can be performed by a processing arrangement and/or a computing arrangement 505. Such processing/computing arrangement 505 can be, for example entirely or a part of, or include, but not limited to, a computer/processor 510 that can include, for example one or more microprocessors, and use instructions stored on a computer-accessible medium (e.g., RAM, ROM, hard drive, or other storage device).

As shown in FIG. 5, for example a computer-accessible medium 515 (e.g., as described herein above, a storage device such as a hard disk, floppy disk, memory stick, CD-ROM, RAM, ROM, etc., or a collection thereof) can be provided (e.g., in communication with the processing arrangement 505). The computer-accessible medium 515 can contain executable instructions 520 thereon. In addition or alternatively, a storage arrangement 525 can be provided separately from the computer-accessible medium 515, which can provide the instructions to the processing arrangement 505 so as to configure the processing arrangement to execute certain exemplary procedures, processes and methods, as described herein above, for example.

Further, the exemplary processing arrangement 505 can be provided with or include an input/output arrangement 535, which can include, for example a wired network, a wireless network, the internet, an intranet, a data collection probe, a sensor, etc. As shown in FIG. 5, the exemplary processing arrangement 505 can be in communication with an exemplary display arrangement 530, which, according to certain exemplary embodiments of the present disclosure, can be a touch-screen configured for inputting information to the processing arrangement in addition to outputting information from the processing arrangement, for example. Further, the exemplary display 530 and/or a storage arrangement 525 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:

1. Leaver A M, Espinoza R, Pirnia T, Joshi S H, Woods R P, Nan K L. Modulation of intrinsic brain activity by electroconvulsive therapy in major depression. Biol Psychiatry Cogn Neurosci Neuroimaging 2016; 1: 77-86. PMID: PMC4750490.
2. Argyelan M, Lencz T, Kaliora S, Sarpal D K, Weissman N, Kingsley P B et al. Subgenual cingulate cortical activity predicts the efficacy of electroconvulsive therapy. Translational psychiatry 2016; 6: e789. PMID: PMC4872412.
3. Fox M D, Liu H, Pascual-Leone A. Identification of reproducible individualized targets for treatment of depression with TMS based on intrinsic connectivity. Neuroimage 2013; 66: 151-160. PMID: PMC3594474.
4. Quitkin, F. M. et al. Use of pattern analysis to identify true drug response. A replication. Arch Gen Psychiatry 44, 259-264 (1987).
5. Papakostas, G. I. Managing partial response or nonresponse: switching, augmentation, and combination strategies for major depressive disorder. J Clin Psychiatry 70 Suppl 6, 16-25, doi:10.4088/JCP.8133su1c.03 (2009).
6. The Practice of Electroconvulsive Therapy: Recommendations for Treatment, Training, and Privileging: A Task Force Report of the American Psychiatric Association. 2nd edn, (2001).
7. O'Reardon, J. P. et al. Efficacy and safety of transcranial magnetic stimulation in the acute treatment of major depression: a multisite randomized controlled trial. Biological psychiatry 62, 1208-1216, doi:10.1016/j.biopsych.2007.01.018 (2007).
8. Horvath, J. C., Mathews, J., Demitrack, M. A. & Pascual-Leone, A. The NeuroStar TMS device: conducting the FDA approved protocol for treatment of depression. J Vis Exp, doi:10.3791/2345 (2010).
9. George, M. S., Taylor, J. J. & Short, E. B. The expanding evidence base for rTMS treatment of depression. Curr Opin Psychiatry 26, 13-18, doi:10.1097/YCO.0b013e32835ab46d (2013).
10. George, M. S. et al. Daily left prefrontal transcranial magnetic stimulation therapy for major depressive disorder: a sham-controlled randomized trial. Arch Gen Psychiatry 67, 507-516, doi:10.1001/archgenpsychiatry.2010.46 (2010).
11. Slotema, C. W., Blom, J. D., Hoek, H. W. & Sommer, I. E. Should we expand the toolbox of psychiatric treatment methods to include Repetitive Transcranial Magnetic Stimulation (rTMS)? A meta-analysis of the efficacy of rTMS in psychiatric disorders. Clin Psychiatry 71, 873-884, doi:10.4088/JCP.08m04872gre (2010).
12. Leaver, A. M. et al. Modulation of intrinsic brain activity by electroconvulsive therapy in major depression. Biol Psychiatry Cogn Neurosci Neuroimaging 1, 77-86, doi: 10.1016/j.bpsc.2015.09.001 (2016).
13. Fox, M. D., Liu, H. & Pascual-Leone, A. Identification of reproducible individualized targets for treatment of depression with TMS based on intrinsic connectivity. NeuroImage 66, 151-160, doi:10.1016/j.neuroimage.2012.10.082 (2013).
14. Drevets, W. C., Savitz, J. & Trimble, M. The subgenual anterior cingulate cortex in mood disorders. CNS spectrums 13, 663-681 (2008).
15. George, M. S. et al. Mood improvement following daily left prefrontal repetitive transcranial magnetic stimulation in patients with depression: a placebo-controlled crossover trial. Am J Psychiatry 154, 1752-1756, doi:10.1176/ajp.154.12.1752 (1997).
16. George M S, W. E., Williams W A, et al. Daily repetitive transcranial magnetic stimulation (rTMS) improves mood in depression. NeuroReport 6, 1853-1856 (1995).
17. Narushima, K., McCormick, L. M., Yamada, T., Thatcher, R. W. & Robinson, R. G. Subgenual cingulate theta activity predicts treatment response of repetitive transcranial magnetic stimulation in participants with vascular depression. J Neuropsychiatry Clin Neurosci 22, 75-84 (2010).
18. Paus, T., Castro-Alamancos, M. A. & Petrides, M. Cortico-cortical connectivity of the human mid-dorsolateral frontal cortex and its modulation by repetitive transcranial magnetic stimulation. The European journal of neuroscience 14, 1405-1411 (2001).
19. Li, X. et al. Acute left prefrontal transcranial magnetic stimulation in depressed patients is associated with immediately increased activity in prefrontal cortical as well as subcortical regions. Biological psychiatry 55, 882-890, doi:10.1016/j.biopsych.2004.01.017 (2004).
20. Teneback, C. C. et al. Changes in prefrontal cortex and paralimbic activity in depression following two weeks of daily left prefrontal TMS. J Neuropsychiatry Clin Neurosci 11, 426-435, doi:10.1176/jnp.11.4.426 (1999).
21. Speer, A. M. et al. Opposite effects of high and low frequency rTMS on regional brain activity in depressed patients. Biological psychiatry 48, 1133-1141 (2000).

22. Mottaghy, F. M. et al. Correlation of cerebral blood flow and treatment effects of repetitive transcranial magnetic stimulation in depressed patients. *Psychiatry Res* 115, 1-14 (2002).
23. Glasser M F, Coalson T S, Robinson E C, Hacker C D, Harwell J, Yacoub E, Ugurbil K, Andersson J, Beckmann C F, Jenkinson M, Smith S M, Van Essen D C. A multi-modal parcellation of human cerebral cortex. Nature. 2016; 536(7615):171-8.
24. Yeo B T, Krienen F M, Sepulcre J, Sabuncu M R, Lashkari D, Hollinshead M, Roffman J L, Smoller J W, Zollei L, Polimeni J R, Fischl B, Liu H, Buckner R L. The organization of the human cerebral cortex estimated by intrinsic functional connectivity. J Neurophysiol. 2011; 106(3):1125-65.

What is claimed is:

1. A non-transitory computer-accessible medium having stored thereon computer-executable instructions for determining at least one effect of at least one convulsive stimulation therapy on at least one patient, wherein, when a computer arrangement executes the instructions, the computer arrangement is configured to perform procedures comprising:
receiving first information related to a visual network of a brain of the at least one patient;
receiving second information related to a default mode network (DMN) of the brain of the at least one patient; and
determining the at least one effect of the at least one convulsive stimulation therapy based on a relationship between the first information and the second information,
wherein the at least one effect of the at least one convulsive stimulation therapy is determined by analyzing a connectivity between the visual network and a connectivity within the DMN.

2. A method for determining at least one effect of at least one convulsive stimulation therapy on at least one patient, comprising:
receiving first information related to a visual network of a brain of the at least one patient;
receiving second information related to a default mode network (DMN) of the brain of the at least one patient; and
using a specifically configured computer hardware arrangement, determining the at least one effect of the at least one convulsive stimulation therapy based on a relation between the first information and the second information,
wherein the at least one effect of the at least one convulsive stimulation therapy is determined by analyzing a connectivity between the visual network and a connectivity within the DMN.

3. The method of claim 2, wherein the at least one convulsive stimulation therapy is at least one of an electroconvulsive therapy or a magnetic seizure therapy.

4. The method of claim 2, wherein the at least one effect of the at least one convulsive stimulation therapy is determined by analyzing a connectivity between the visual network and a region of a dorsolateral prefrontal cortex (DLPFC) that is anti-correlated to the DMN.

5. The method of claim 4, wherein the connectivity being determined is a functional connectivity.

6. The method of claim 2, wherein the at least one effect of the at least one convulsive stimulation therapy is determined by analyzing a connectivity between the visual network and regions of the DMN.

7. The method of claim 4, wherein the connectivity being determined is an anatomical connectivity.

8. The method of claim 4, wherein the connectivity is based on white matter tracts in at least one of the visual network or the DMN.

9. The method of claim 4, wherein the connectivity is determined based on a diffusion tensor imaging procedure.

10. The method of claim 2, further comprising:
receiving third information related to a dorsolateral prefrontal cortex (DLPFC) of the brain; and
determining the at least one effect of the at least one convulsive stimulation therapy based on a further relationship between the first information and the third information.

11. The method of claim 10, wherein the DLPFC is coupled to the DMN.

12. The method of claim 10, wherein the DLPFC is negatively coupled to the DMN.

13. The method of claim 2, wherein the at least one effect includes a response of the at least one patient to the at least one convulsive therapy.

14. The method of claim 13, wherein the response is a positive response.

15. The method of claim 2, wherein at least one of the first information or the second information is received from a magnetic resonance imaging (MRI) apparatus.

16. The method of claim 15, wherein the MRI apparatus is a functional MRI apparatus.

17. The method of claim 2, further comprising:
generating third information based on the relationship between the first information and the second information; and
determining the at least one effect by comparing the third information to fourth information that is related to a previous determination of the at least one effect on a plurality of further brains of a plurality of further patients.

18. A method for determining at least one effect of at least one convulsive stimulation therapy on at least one patient, comprising:
receiving first information related to a visual network of a brain of the at least one patient;
receiving second information related to a default mode network (DMN) of the brain of the at least one patient; and
using a specifically configured computer hardware arrangement, determining the at least one effect of the at least one convulsive stimulation therapy based on a relation between the first information and the second information, wherein the at least one effect is determined based on at least one visual covariate.

19. A system for determining at least one effect of at least one convulsive stimulation therapy on at least one patient, comprising:
a computer hardware arrangement specifically configured to:
receive first information related to a visual network of a brain of the at least one patient;
receive second information related to a default mode (DMN) of the brain of the at least one patient; and
determine the at least one effect of the at least one convulsive stimulation therapy based on a relation between the first information and the second information,
wherein the at least one effect of the at least one convulsive stimulation therapy is determined by analyzing a connectivity between the visual network and a connectivity within the DMN.

20. A non-transitory computer-accessible medium having stored thereon computer-executable instructions for determining at least one effect of at least one convulsive stimulation therapy on at least one patient, wherein, when a computer arrangement executes the instructions, the computer arrangement is configured to perform procedures comprising:
   receiving first information related to a visual network of a brain of the at least one patient;
   receiving second information related to a default mode network (DMN) of the brain of the at least one patient; and
   determining the at least one effect of the at least one convulsive stimulation therapy based on a relationship between the first information and the second information, wherein the at least one effect is determined based on at least one visual covariate.

21. A system for determining at least one effect of at least one convulsive stimulation therapy on at least one patient, comprising:
   a computer hardware arrangement specifically configured to:
      receive first information related to a visual network of a brain of the at least one patient;
      receive second information related to a default mode (DMN) of the brain of the at least one patient; and
      determine the at least one effect of the at least one convulsive stimulation therapy based on a relation between the first information and the second information, wherein the at least one effect is determined based on at least one visual covariate.

* * * * *